United States Patent
Kwon et al.

(10) Patent No.: US 11,052,048 B2
(45) Date of Patent: Jul. 6, 2021

(54) ESOMEPRAZOLE-CONTAINING COMPLEX CAPSULE AND PREPARATION METHOD THEREFOR

(71) Applicant: HANMI PHARM. CO., LTD., Hwaseong-si (KR)

(72) Inventors: Taek Kwan Kwon, Suwon-si (KR); Seung Hun Chang, Anyang-si (KR); Ho Taek Im, Yongin-si (KR); Yong Il Kim, Suwon-si (KR); Jae Hyun Park, Suwon-si (KR); Jong Soo Woo, Seoul (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 16/345,456

(22) PCT Filed: Oct. 19, 2017

(86) PCT No.: PCT/KR2017/011571
§ 371 (c)(1),
(2) Date: Apr. 26, 2019

(87) PCT Pub. No.: WO2018/080104
PCT Pub. Date: May 3, 2018

(65) Prior Publication Data
US 2019/0247316 A1    Aug. 15, 2019

(30) Foreign Application Priority Data

Oct. 28, 2016  (KR) .................. 10-2016-0142156

(51) Int. Cl.
*A61K 9/48*   (2006.01)
*A61P 1/04*   (2006.01)
*A61K 31/4439*  (2006.01)
*A61K 9/50*   (2006.01)

(52) U.S. Cl.
CPC .............. *A61K 9/4808* (2013.01); *A61K 9/48* (2013.01); *A61K 9/4825* (2013.01); *A61K 9/4833* (2013.01); *A61K 9/4891* (2013.01); *A61K 9/50* (2013.01); *A61K 31/4439* (2013.01); *A61P 1/04* (2018.01)

(58) Field of Classification Search
None
See application file for complete search history.

(56) References Cited

U.S. PATENT DOCUMENTS

| | | |
|---|---|---|
| 5,817,338 A | 10/1998 | Bergstrand et al. |
| 2008/0003281 A1 | 1/2008 | Clemmensen et al. |
| 2010/0272798 A1* | 10/2010 | Akiyama ............. A61K 9/5078 424/461 |
| 2016/0128945 A1 | 5/2016 | Akiyama et al. |

FOREIGN PATENT DOCUMENTS

| | | | |
|---|---|---|---|
| CN | 101884629 A | 11/2010 | |
| CN | 102100671 A | 6/2011 | |
| CN | 102670521 A | 9/2012 | |
| CN | 102940611 A | 2/2013 | |
| CN | 103040774 A | 4/2013 | |
| CN | 104940170 A | 9/2015 | |
| EP | 2 319 504 A1 | 5/2011 | |
| KR | 10-1996-0704532 A | 10/1996 | |
| KR | 10-2007-0083956 A | 8/2007 | |
| KR | 10-1401913 B1 | 5/2014 | |
| WO | 2005/009410 A2 | 2/2005 | |
| WO | WO-2005051362 A2 * | 6/2005 | ......... A61K 31/4439 |
| WO | 2012/001705 A2 | 1/2012 | |

OTHER PUBLICATIONS

Seema Thakral et al. "Eudragit: a technology evaluation", Expert Opinion on Drug Delivery, vol. 10, No. 1, Oct. 26, 2012, pp. 131-149 (20 pages total).
Inderbir Singh et al, "Formulation and evaluation of press coated tablets of esomeprazole for colonic delivery", Asian Journal of Pharmaceutics, vol. 6, No. 4, 2012, pp. 252-258 (9 pages total).
Office Action dated Jan. 25, 2021 in Chinese Application No. 201780067122.4.
Yu Fang et al., "Eudragit L/HPMCAS Blend Enteric-Coated Lansoprazole Pellets: Enhanced Drug Stability and Oral Bioavailability," AAPS PharmSciTech, Jun. 2014, pp. 513-521 (10 pages), vol. 15, No. 3.
Korean Intellectual Property Office, Office Action issued in KR 10-2016-0142156 dated May 18, 2018.
Korean Intellectual Property Office, Office Action issued in KR 10-2016-0142156 dated Jul. 21, 2017.
International Search Report of PCT/KR2017/011571 dated Jan. 31, 2018.

* cited by examiner

*Primary Examiner* — H. Sarah Park
(74) *Attorney, Agent, or Firm* — Sughrue Mion, PLLC

(57) ABSTRACT

Provided are a composite capsule and a method of preparing the composite capsule. The composite capsule includes a first dissolving part including a core, an inner coating layer on the core, and a first enteric coating layer on the inner coating layer, wherein core contains, as an active ingredient, esomeprazole or a pharmaceutically acceptable salt thereof. The composite capsule further includes a second dissolving part including a core, which contains, as an active ingredient, esomeprazole or a pharmaceutically acceptable salt thereof, an inner coating layer on the core, and a second enteric coating layer on the inner coating layer.

11 Claims, 6 Drawing Sheets

【Figure 1】
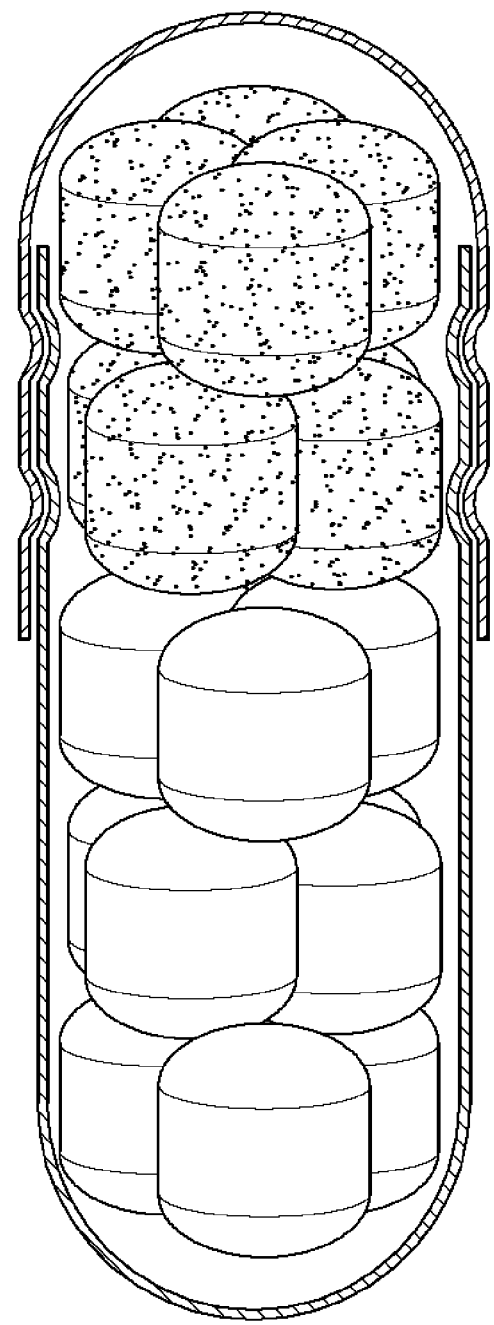

【Figure 2】
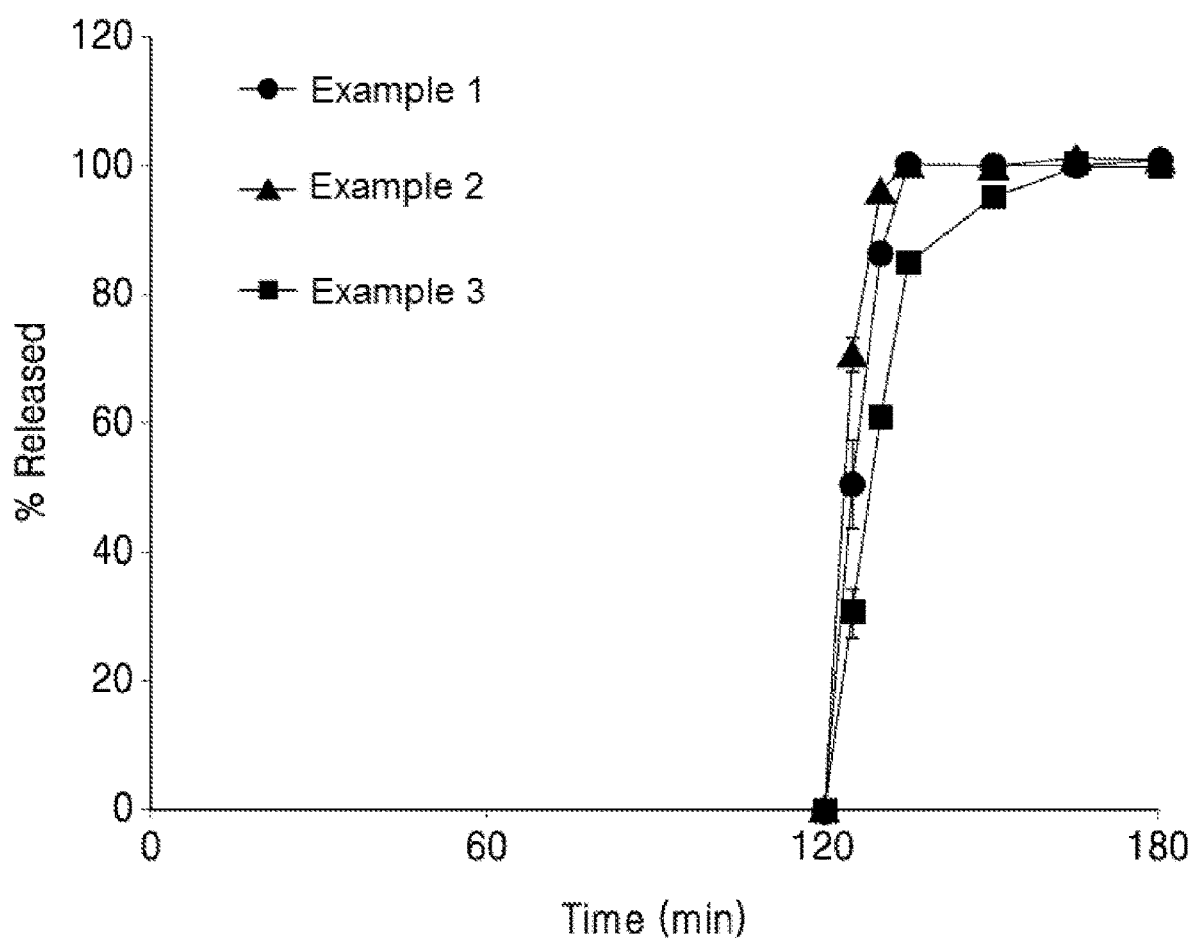

[Figure 3]
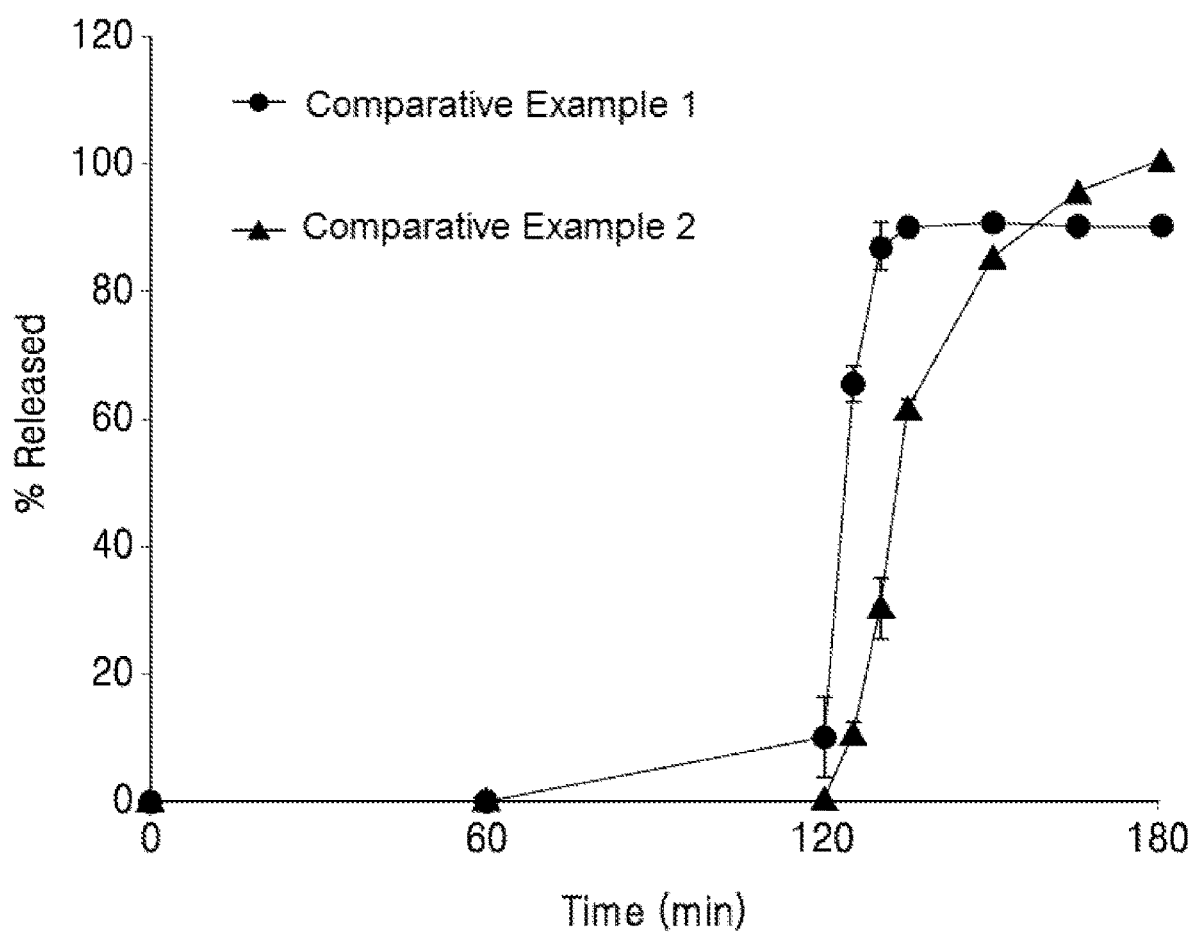

[Figure 4]
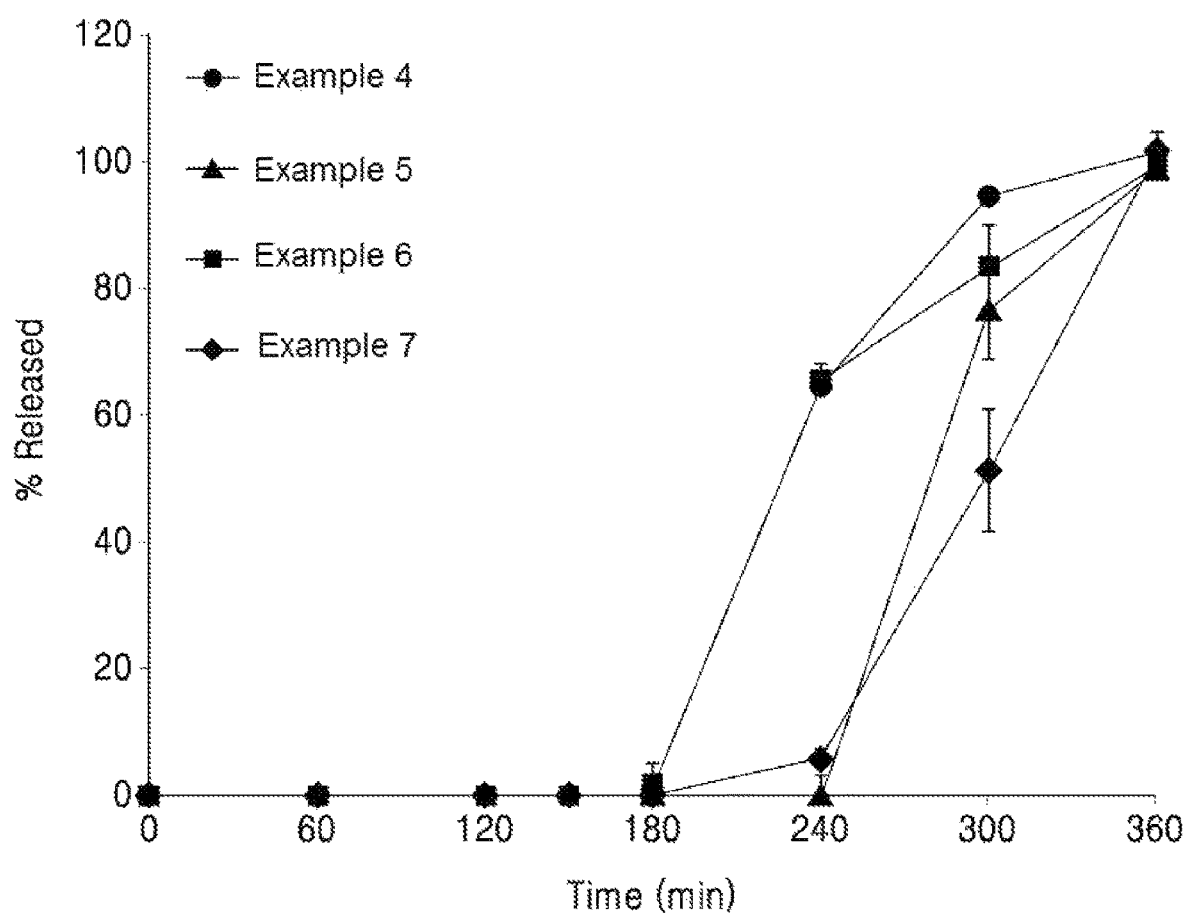

[Figure 5]
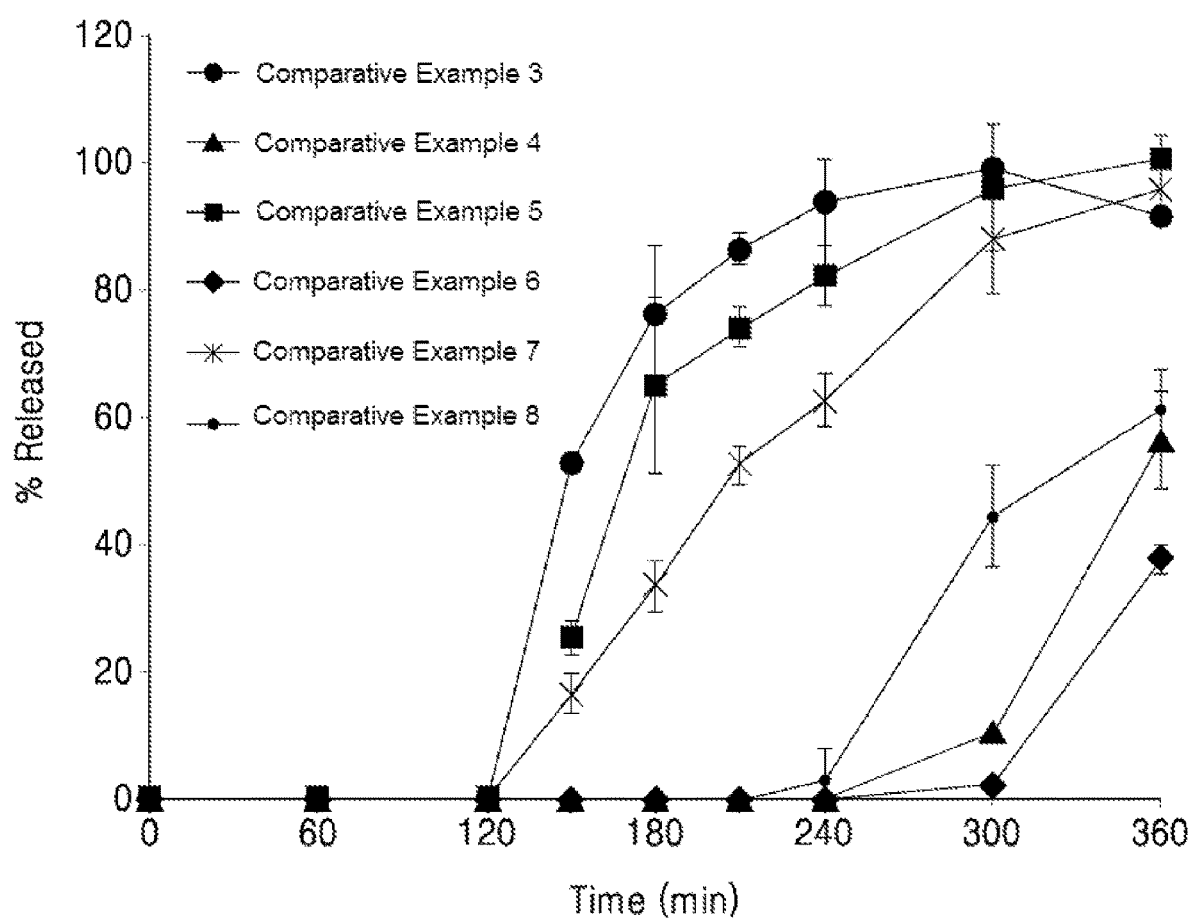

【Figure 6】
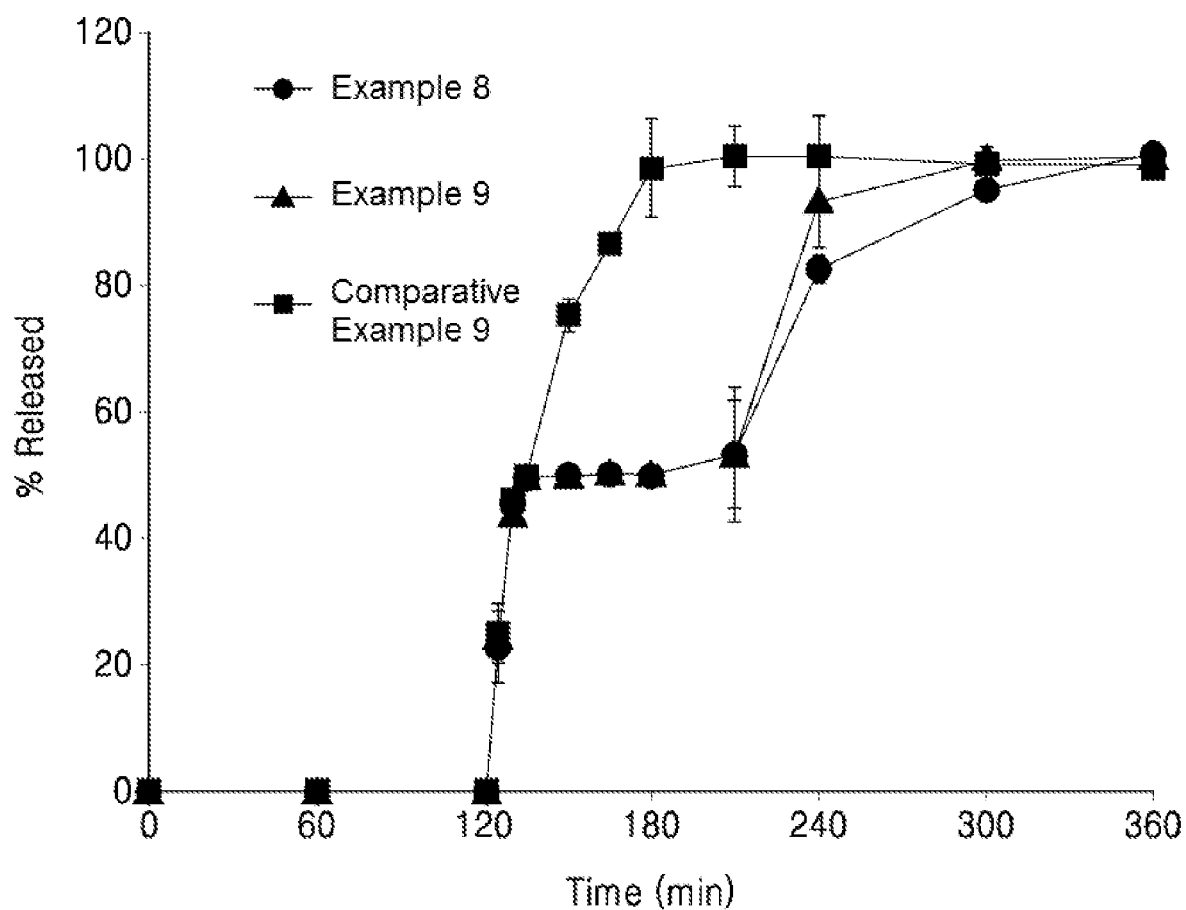

US 11,052,048 B2

ESOMEPRAZOLE-CONTAINING COMPLEX CAPSULE AND PREPARATION METHOD THEREFOR

CROSS REFERENCE TO RELATED APPLICATIONS

This application is a National Stage of International Application No. PCT/KR2017/011571 filed Oct. 19, 2017, claiming priority based on Korean Patent Application No. 10-2016-0142156 filed Oct. 28, 2016.

TECHNICAL FIELD

The present disclosure relates to an esomeprazole-containing composite capsule and a method of preparing the same, and more particularly, to an esomeprazole-containing composite capsule that is enteric in that an active ingredient thereof is not dissolved in the stomach and double release characteristics are exhibited in the intestines, so as to enable release of the active ingredient for a prolonged period of time and to sustain a medicinal effect, and a method of preparing the esomeprazole-containing composite capsule.

BACKGROUND ART

Esomeprazole((S)-5-methoxy-2-[(4-methoxy-3,5-dimethylpyridine-2-yl)methylsulfinyl]-3H-benzoimidazole), which is the (S)-optical isomer known to have excellent safety and efficacy among the two optical isomers of omeprazole, is one type of proton pump inhibitor (PPI).

As a PPI, esomeprazole has an effect of inhibiting gastric acid secretion in mammals including humans by regulating gastric acid secretion at the last stage of the acid secretion pathway. Accordingly, esomeprazole is widely known to be used for the prevention and treatment of diseases related to hypersecretion of gastric acid, such as gastroesophageal reflux disease including reflux esophagitis, gastritis, duodenitis, gastric ulcer, duodenal ulcer, and peptic ulcer, and the like.

PPIs including esomeprazole are readily degraded or modified under acidic conditions. Thus, enteric formulations have been developed which can prevent decomposition of drugs through the introduction of an enteric coating layer which prevents exposure to gastric acid in the stomach, and which can be dissolved and absorbed in the intestines.

In addition, esomeprazole agents in the art have been found to have problems in that, due to a short duration time, gastric acid is secreted after 12 hours or more of taking a dosage of an esomeprazole agent, and symptoms such as heartburn are observed due to a pH drop in the stomach. To prevent this phenomenon, the frequency of administration of medicines can be increased. However, increasing the frequency of administration of medicines can cause a problem in that the medication compliance of patients is lowered.

DESCRIPTION OF EMBODIMENTS

Technical Problem

Therefore, development of an esomeprazole-containing oral dosage form having acid resistance while exhibiting more sustained drug efficacy is necessary.

Provided is an esomeprazole-containing composite capsule which is resistant to acid such that is not degraded in the stomach, and has double-release characteristics leading to sustained drug efficacy.

Provided is a method of preparing the esomeprazole-containing composite capsule.

Solution to Problem

An aspect of the present disclosure provides a composite capsule comprising:

a first dissolving part comprising a core comprising, as an active ingredient, esomeprazole or a pharmaceutically acceptable salt thereof, an inner coating layer on the core, and a first enteric coating layer on the inner coating layer; and a second dissolving part comprising a core comprising, as an active ingredient, esomeprazole or a pharmaceutically acceptable salt thereof, an inner coating layer on the core, and a second enteric coating layer on the inner coating layer, wherein the first enteric coating layer comprises, as a coating base material, methacrylic acid copolymer LD in an amount of about 5% (w/w) to about 50% (w/w) of the core on which the inner coating layer is formed, and the second enteric coating layer comprises, as a coating base material, a mixture containing methacrylic acid copolymer S and methacrylic acid copolymer L at a ratio of about 1.5:1 (w/w) to about 3.5:1 (w/w) in an amount of about 15% (w/w) to about 40% (w/w) of the core on which the inner coating layer is formed.

Another aspect of the present disclosure provides a method of preparing the composite capsule of any one of claims 1 to 13, the method comprising:

preparing a core comprising esomeprazole or a pharmaceutically acceptable salt thereof, and a pharmaceutical additive;

coating the core with an inner coating layer;

obtaining a first dissolving part by coating a first enteric coating layer on the inner coating layer;

separately, obtaining a second dissolving part by coating a second enteric coating layer on the inner coating layer; and filling a capsule with the first dissolving part and the second dissolving part together, wherein the first enteric coating layer comprises, as a coating base material, methacrylic acid copolymer LD in an amount of about 5% (w/w) to about 50% (w/w) of the core on which the inner coating layer is formed, and the second enteric coating layer comprises, as a coating base material, a mixture containing methacrylic acid copolymer S and methacrylic acid copolymer L at a ratio of about 1.5:1 (w/w) to about 3.5:1 (w/w) in an amount of about 15% (w/w) to about 40% (w/w) of the core on which the inner coating layer is formed.

Advantageous Effects of Disclosure

An esomeprazole-containing composite capsule according to an embodiment has acid resistance and is not susceptible to degradation due to exposure to gastric juice, and further, is able to exhibit sustained drug efficacy for a long time by including both a first dissolving part which enables immediate release upon reaching the intestines and a second dissolving part which enables delayed release. Therefore, when administered once a day, the esomeprazole-containing composite capsule can exhibit sustained drug efficacy without any side effects including heartburn after 12 hours of administration once a day.

BRIEF DESCRIPTION OF DRAWINGS

FIG. 1 is a schematic diagram of a composite capsule according to an embodiment in which both a core (dotted) of a first dissolving part and a core (undotted) of a second dissolving part are mini-tablets.

FIGS. 2 and 3 are graphs showing dissolution test results of first enteric coating layer-forming mini-tablets of Examples 1 to 3 and Comparative Examples 1 and 2, respectively.

FIGS. 4 and 5 are graphs showing dissolution test results of second enteric coating layer-forming mini-tablets of Examples 4 to 7 and Comparative Examples 3 to 8, respectively.

FIG. 6 is a graph showing measurement results of dissolution tests of composite capsules of Examples 8 and 9 and Comparative Example 9.

MODE OF DISCLOSURE

Hereinafter, the present disclosure will be described in detail.

All the technical terms used in the present invention are, unless otherwise described, meant to be the same as being generally understood by one of ordinary skill in the art. In addition, preferred methods or samples are described in the present specification, but similar or equivalent ones are also included in the scope of the present invention. In addition, numerical values set forth herein are considered to including the meaning of "about", even if it is not explicated stated. The contents of all publications referred in the present specification are incorporated herein by reference in their entireties.

According to an embodiment, provided there is a composite capsule comprising:

a first dissolving part comprising a core comprising, as an active ingredient, esomeprazole or a pharmaceutically acceptable salt thereof, an inner-coating layer on the core, and a first enteric coating layer on the inner-coating layer; and a second dissolving part comprising a core comprising, as an active ingredient, esomeprazole or a pharmaceutically acceptable salt thereof, an inner-coating layer on the core, and a second enteric coating layer on the inner-coating layer, wherein the first enteric coating layer may comprise, as a coating base material, methacrylic acid copolymer LD in an amount of about 5% (w/w) to about 50% (w/w) of the core on which the inner-coating layer is formed, and the second enteric coating layer may comprise, as a coating base material, a mixture containing methacrylic acid copolymer S and methacrylic acid copolymer L at a ratio of about 1.5:1 (w/w) to about 3.5:1 (w/w) in an amount of about 15% (w/w) to about 40% (w/w) of the core on which the inner-coating layer.

The pharmaceutically acceptable salt of esomeprazole may be any pharmaceutically acceptable salt available in the art, and for example, may be a metal salt, such as a magnesium (Mg) salt, a strontium (Sr) salt, a lithium salt, a sodium salt, a potassium salt, a calcium salt, or the like, or an ammonium salt. However, the pharmaceutically acceptable salt of esomeprazole is not limited thereto. In one embodiment, the pharmaceutically acceptable salt thereof may be a Mg salt of esomeprazole or a Sr salt of esomeprazole.

In addition, the esomeprazole or the pharmaceutically acceptable salt thereof may be used in the form of anhydride or hydrate.

The core comprising the esomeprazole or the pharmaceutically acceptable salt thereof may be any solid agent that can be included in a capsule, and for example, may be selected from pellets, mini-tablets, tablets, and a combination thereof. In one embodiment, the core may include a mini-tablet, and more specifically, may have a mini-tablet form close to a spherical shape. Thus, the first dissolving part and/or the second dissolving part, as multi-unit spherical tablets (MUSTs), may be filled in the composite capsule. In one embodiment, the core of the first dissolving part and the core of the second dissolving part may be both in a mini-tablet form, and as MUSTs, the both cores may be filled in the composite capsule (FIG. 1).

The mini-tablet may have a diameter of 1 mm to 4 mm, and more specifically, a diameter of 1.5 mm to 3 mm. The first dissolving part and the second dissolving part in the capsule interior space may be filled with mini-tablets separated by at least 4, more specifically, 4 to 40 independent layers, respectively. The mini-tablet may be prepared according to methods known in the art.

The core may comprise, along with esomeprazole or a pharmaceutically acceptable salt thereof, which is an active ingredient, any suitable pharmaceutical additive available in the art for the preparation of the core. For example, the core may additionally comprise one or more additives selected from a diluent, a binder, a disintegrant, a lubricant, a surfactant, an anti-oxidants, a preservative, a stabilizer, and a combination thereof. However, the additive is not limited thereto.

For use as the diluent, one or more diluents may be selected from mannitol, microcrystalline cellulose, lactose, cellulose and a derivative thereof, dibasic or tribasic calcium phosphate, erythritol, low-substituted hydroxypropyl cellulose (HPC-L), pregelatinized starch, sorbitol, xylitol, and a combination thereof, but the diluent is not limited thereto. In one embodiment, for use as the diluent, mannitol and/or microcrystalline cellulose may be used.

For use as the binder, one or more binders may be selected from hydroxypropyl cellulose (HPC), copovidone (a copolymer of vinylpyrrolidone with other vinyl derivatives), hydroxypropyl methylcellulose (HPMC), polyvinylpyrrolidone (povidone), pregelatinized starch, HPC-L, and a combination thereof, but the binder is not limited thereto. In one embodiment, for use as the binder, HPC may be used.

For use as the disintegrant, one or more disintegrants may be croscarmellose sodium, corn starch, crospovidone, HPC-L, pregelatinized starch, and a combination thereof, but the disintegrant is not limited thereto. In one embodiment, for use as the disintegrant, croscarmellose sodium may be used.

For use as the lubricant, one or more selected from sodium stearyl fumarate, magnesium stearate, talc, polyethyleneglycol, calcium behenate, calcium stearate, hydrogenated castor oil, and a combination thereof, but the lubricant is not limited thereto. In one embodiment, for use as the lubricant, sodium stearyl fumarate may be used.

The inner-coating layer formed on the core is capable of preventing an interaction between the core and the enteric coating layer and may include, as a coating base material, a hydrophilic polymer that does not inhibit the release of the active ingredient in the core upon collapse of the enteric coating layer after administration of the composite capsule. The coating base material of the inner-coating layer may be, for example, at least one selected from HPMC, polyvinylpyrrolidone (PVP), HPC-L, starch, gelatin, ethyl cellulose (EC), and a combination thereof. In one embodiment, the inner-coating layer may include HPMC as the coating base material.

In the present specification, the core on which the inner-coating layer is formed is also referred to as an inner-coated core. An amount of the inner-coating layer may be appropriately selected from by one of ordinary skill in the art, but in one embodiment, the amount of the inner-coating layer may be in a range of about 3 weight % to about 5 weight % based on the inner-coated core.

The first dissolving part and the second dissolving part of the composite capsule both include the enteric coating layers, and thus the acid resistance can be secured in the stomach. In addition, upon reaching the intestines through the stomach, the first release of the active ingredient is rapidly done from the first dissolving part, and after the delayed time, the second release of the active ingredient is sequentially done from the second dissolving part. Therefore, the composite capsule may avoid drug degradation in the stomach, and due to the rapid dissolution of the drug upon reaching the intestines, can exhibit fast drug efficacy, and the drug efficacy may be then sustained for a long time by the double release of the drug.

The enteric coating layer included in the first dissolving part may include, as a coating base materials, methacrylic acid copolymer LD. The methacrylic acid copolymer LD is an anionic copolymer including methacrylic acid and ethylacrylate at a ratio of about 1:1, and is present in the form of a solution. The methacrylic acid copolymer LD is commercially available under the trade name of Eudragit L30 D-55, and the IUPAC name thereof is poly(methacylic acid-co-ethyl acrylate) 1:1.

The enteric coating layer included in the first dissolving part may include, as a coating base materials, a mixture containing methacrylic acid copolymer S and methacrylic acid copolymer L at a ratio of about 1.5:1 (w/w) to about 3.5:1 (w/w), for example, about 2:1 (w/w) to about 3:1 (w/w).

The methacrylic acid copolymer S is an anionic copolymer including methacrylic acid and methyl methacrylate at a ratio of about 1:2. The methacrylic acid copolymer S is commercially available under the trade name of Eudragit S-100, and the IUPAC name thereof is poly(methacylic acid-co-methyl methacrylate) 1:2.

The methacrylic acid copolymer L is an anionic copolymer including methacrylic acid and methyl methacrylate at a ratio of about 1:1. methacrylic acid copolymer L is commercially available under the trade name of Eudragit L-100, and the IUPAC name thereof is poly(methacylic acid-co-methyl methacrylate) 1:1.

The methacylic acid copolymer LD, which is the coating base material of the enteric coating layer of the first dissolving part (also, referred to as the first enteric coating layer), is a solid powder included in an amount of about 5% (w/w) to about 50% (w/w), for example, about 8% (w/w) to about 30% (w/w), with respect to the inner-coated core of the first dissolving part. When the amount of such a solid powder is less than 5% (w/w) with respect to the inner-coated core, it is difficult to secure acid resistance in the 0.1 N HCl aqueous solution, in spite of rapid dissolution of the solid powder. In this regard, when orally administered, the active ingredient may be degraded due to the nature of the PPIs, and accordingly, the medical efficacy may be exhibited with difficulty. In addition, when the methacrylic acid copolymer LD is used as a solid powder for the coating in an amount of greater of 50% (w/w) with respect to the inner-coated core of the first dissolving part, the sufficient acid resistance may be secured in the 0.1 N HCl aqueous solution, but after passing through the stomach, the dissolution of the active ingredient is excessively slowed in the intestines, resulting in a delay in the drug absorption in the living body and a delayed medical efficacy.

The methacrylic acid copolymer S and the methacrylic acid copolymer L, which are the coating base materials of the enteric coating layer of the second dissolving part (also, referred to as the second enteric coating layer), may be mixed at a ratio of about 1.5:1 (w/w) to about 3.5:1 (w/w), and for example, about 2:1 (w/w) to about 3:1 (w/w). When the coating base materials are mixed at a ratio lower than the ratio above, a proportion of the methacrylic acid copolymer L, which is dissolved at a relatively low pH, becomes relatively high, and accordingly, its rapid release may occur upon reaching the intestines through the stomach, resulting in difficult expression of characteristics of the double release. In addition, when the coating base materials are mixed at a ratio higher than the ratio above, a proportion of the methacrylic acid copolymer S, which is a relatively insoluble substance, is increased, resulting in excessively delayed release of the drugs. In this regard, the coating base materials may be excreted without achieving complete releasing of the drugs, resulting in low bioavailability.

As a solid powder, the mixture containing the methacrylic acid copolymer S and the methacrylic acid copolymer L may be used in an amount of 15% (w/w) to 40% (w/w), for example, 20% (w/w) to 35% (w/w), with respect to the inner-coated core. When the mixture is contained in an amount less than the amount above, the second dissolving part may not be able to secure a desired delay in the dissolution, and due to the fast dissolution upon reaching the intestines, the double release characteristics may not be secured with difficulty. In addition, when the mixture is contained in an amount greater than the amount above, the enteric coating layer may become thicker so that the second release of the drugs from the dissolving member may be excessively delayed. Thus, drugs in the composite capsule may be excreted without achieving complete releasing of the drugs, resulting in low bioavailability.

The composite capsule may include the active ingredient separately in the first dissolving part and the second dissolving part at an appropriate ratio, and such an appropriate ratio may be selected from by one of ordinary skill in the art depending on the desired dissolution characteristics. In one embodiment, as a free base, esomeprazole or a pharmaceutically acceptable salt thereof may be included at a weight ratio of 2:1 to 1:2 between the first dissolving part and the second dissolving part in the composite capsule.

The capsule constituting the composite capsule may be a hard capsule, and any hard capsule available in the art may be used. A base material of the hard capsule may be, for example, selected from gelatin, hypromellose, pullulan (NP caps TM or the like, Capsugel Company), polyvinyl alcohol, and a combination thereof, but the base material is not limited thereto.

For use as the hard capsule, any conventional sized capsule available in the art may be used. Depending on the size of the capsule, a variety of capsule sizes are used. A large-sized capsule, for example, size 00 capsule (having a diameter of a capsule cap of 8.5 mm and a length of a capsule: 23.3 mm) is inconvenient for elderly patients or young children who have small body sizes, and may also have poor portability due to an increased capsule volume. In one embodiment, considering mass limits of tablets or granules to be filled in a capsule, the composite capsule of size 0, size 1, size 2, size 3, or size 4, for example, size of 1, size of 2, or size of 3 may be used.

In the composite capsule, the active ingredient is hardly released in the strongly acidic environment. However, the first release of the active ingredient rapidly proceeds from the first dissolving part in the intestines at a pH of 5.5 or less, and the second release of the active ingredient proceeds from the second dissolving part in the intestines at a pH of 6.5 to 7.0.

Regarding the dissolution test on the composite capsule, the composite capsule is left for 2 hours in 0.1 N HCl aqueous solution, and then, the solution was transferred an artificial intestinal fluid at a pH of 6.7 to 6.9. In the dissolution test, the release is hardly occurred during the first two hours, but the release starts in the artificial intestinal fluid. After 150 minutes of the start of the dissolution test, the first release in which about 90% (w/w) or more of the active ingredient of the first dissolving part is released is performed from the first dissolving part. After a delay time of 180 minutes has elapsed from the start of the dissolution test, the dissolution of the active ingredient starts from the second dissolving part, and then, at 360 minutes, the second release in which the dissolution is completed (about 99% or more) is achieved. During the delay time of 180 minutes, 5% of the active ingredient, preferably, 2% of the active ingredient, of the second dissolving part may be achieved.

In one embodiment, when a dissolution test is continuously conducted for 240 minutes in an artificial intestinal fluid having a pH of 6.7 to 6.9 following dissolution in 0.1 N HCl aqueous solution at 100 revolutions per minutes (rpm) for 120 minutes at a temperature of 37±0.5° C. according to the paddle method II described in the United States Pharmacopeia (USP), the composite capsule has acid resistance in 0.1 N HCl for 120 minutes, about 55% or less of the active ingredient is dissolved in the artificial intestinal fluid for 60 minutes, and about 95% or more of the active ingredient is dissolved in the artificial intestinal fluid for 240 minutes (see Experimental Example 4).

Thus, considering that the composite capsule may be able to have sufficient bioavailability and duration time by not dissolving the active ingredient in the stomach, but double-releasing the active ingredient in the intestines, the composite capsule can be effectively used while reducing the frequency of administration.

The composite capsule may include, as an active ingredient, esomeprazole or a pharmaceutically acceptable salt thereof. Such an active ingredient is known to be effective, or can be used for any treatment or prevention of diseases for which medicine is efficacious to be newly discovered in the future. Therefore, according to an embodiment, the composite capsule may be used for prevention of treatment of diseases related to hypersecretion of gastric acid selected from gastroesophageal reflux disease, gastritis, duodenitis, gastric ulcer, duodenal ulcer, and peptic ulcer.

In one embodiment, the composite capsule can be administered once a day.

Another aspect of the present disclosure provides a method of preparing the composite capsule of any one of claims 1 to 13, the method comprising:

preparing a core comprising esomeprazole or a pharmaceutically acceptable salt thereof, and a pharmaceutical additive;

coating the core with an inner-coating layer;

obtaining a first dissolving part by coating a first enteric coating layer on the inner-coating layer;

separately, obtaining a second dissolving part by coating a second enteric coating layer on the inner-coating layer; and filling a capsule together with the first dissolving part and the second dissolving part, wherein the first enteric coating layer comprises, as a coating base material, methacrylic acid copolymer LD in an amount of about 5% (w/w) to about 50% (w/w) of the core on which the inner-coating layer is formed, and the second enteric coating layer comprises, as a coating base material, a mixture containing methacrylic acid copolymer S and methacrylic acid copolymer L at a ratio of about 1.5:1 (w/w) to about 3.5:1 (w/w) in an amount of about 15% (w/w) to about 40% (w/w) of the core on which the inner-coating layer.

Details of a method of preparing oral solid preparation according to an embodiment may be applied as it is for the oral solid preparation according to the aspect above of the present disclosure, and any preparation method known in the art may be used for the detailed.

When the cores of the first dissolving part and the second dissolving part of the composite capsule are mini-tablets (MUSTs) or regular tablets, the cores may be prepared according to direct compression or indirect compression. For the direct compression, dry granules or wet granules may be used.

In one embodiment, the preparing of the core may comprise the following steps:

(a) mixing diluents with esomeprazole or a pharmaceutically acceptable salt thereof;

(b) mixing the mixture of step (a) with a disintegrant, a binder, and a lubricant; and (c) subjecting the mixture of step (b) to dry granulation, followed by tableting the resulting product to obtain a mini-tablet or a tablet.

To coat the mini-tablet or the tablet with the inner-coating layer, the first enteric coating layer, and the second enteric coating layer, any coating method of coating a mini-tablet or a tablet may be applied. For example, a fluidized-bed coater may be used for the coating.

hereinafter, the present invention will be described in detail with reference to Examples below. However, Examples below are illustrative examples of embodiments and are not intended to otherwise limit the scope of embodiments in any way.

EXAMPLES

Preparation Example 1: Formation of Esomeprazole Magnesium Salt-Containing Core and Inner-Coating Layer Using the compositions in Table 1 below, an esomeprazole magnesium salt and mannitol were mixed, and the mixture was sieved using a 30 mesh round sieve. The resulting product was added to an empty blender with microcrystalline cellulose, croscarmellose sodium, hydroxypropylcellulose, and sodium stearyl fumarate to be blended for 15 minutes, thereby preparing a final mixture. The final mixture was put into a roller compactor, and then, subjected to dry granulation. Granules obtained therefrom were sieved using a 20 mesh round sieve.

Next, a MUST punch having a diameter of 2.0 mm was used to tablet 10 mini-tablets each having a pressure at a degree of about 1 kp to about 2 kp and a weight of 7.5 mg, thereby forming MUSTs.

TABLE 1

Compositions of esomeprazole magnesium salt-containing core

| | Ingredient | Weight (mg/10 tablets) | Weight (%) |
|---|---|---|---|
| Core | Esomeprazole magnesium salt | 21.7 | 28.9 |
| | Microcrystalline cellulose | 15.0 | 20.0 |

TABLE 1-continued

Compositions of esomeprazole magnesium salt-containing core

| Ingredient | Weight (mg/10 tablets) | Weight (%) |
|---|---|---|
| Mannitol | 30.5 | 40.7 |
| Croscarmellose sodium | 2.4 | 3.2 |
| Hydroxypropylcellulose | 2.4 | 3.2 |
| Sodium stearyl fumarate | 3.0 | 4.0 |
| Sum | 75.0 | 100.0 |

The prepared MUSTs were coated with a coating fluid having compositions of Table 2 below in a fluidized-bed coater, thereby obtaining inner-coated mini-tablets having a weight of 7.88 mg per tablet.

TABLE 2

Compositions of inner-coating layer

| | Ingredient | Weight (mg/10 tablets) | Weight (%) |
|---|---|---|---|
| Separable coating layer | Hydroxypropyl-cellulose | 3.8 | 4.82 |
| | Purified water | (suitable amount, q.s.) | — |
| | Sum | 78.8 | 100.0 |

Preparation Example 2: Examples 1 to 3 and Comparative Examples 1 and 2

Preparation of a Mini-Tablet Forming a First Enteric Coating Layer

Using the compositions of Table 3 in a fluidized bed granulator, the inner-coated mini-tablet was coated, so as to prepare a mini-table forming a first enteric coating layer according to Examples 1 to 3 and Comparative Examples 1 and 2. In Examples 1 to 3, Eudragit L30 D-55, which is a first enteric coating base material, was coated at a weight of 5% (w/w) to 50% (w/w) with respect to the inner-coated mini-tablet. In Comparative Examples 1 and 2, Eudragit L30 D-55 was each coated at a weight of 4% (w/w) and 51% (w/w), respectively.

TABLE 3

Compositions of first enteric coating layer

| | Weight (mg/10 tablets) | | | | |
|---|---|---|---|---|---|
| Ingredient | Example 1 | Example 2 | Example 3 | Comparative Example 1 | Comparative Example 2 |
| Eudragit L30 D-55 (as solid powder) | 26.35 (7.88) | 13.18 (3.94) | 131.80 (39.40) | 10.54 (3.15) | 132.59 (40.19) |
| Triethyl citrate | 2.35 | 1.18 | 11.80 | 0.94 | 12.59 |

TABLE 3-continued

Compositions of first enteric coating layer

| | Weight (mg/10 tablets) | | | | |
|---|---|---|---|---|---|
| Ingredient | Example 1 | Example 2 | Example 3 | Comparative Example 1 | Comparative Example 2 |
| Diacetylated monoglyceride | 0.43 | 0.22 | 2.20 | 0.17 | 2.99 |
| Polysorbate 80 | 0.18 | 0.09 | 0.90 | 0.07 | 1.69 |
| Purified water | (q.s.) | (q.s.) | (q.s.) | (q.s.) | (q.s.) |
| Sum | 108.11 | 93.47 | 225.50 | 90.52 | 228.66 |

Preparation Example 3: Examples 4 to 7 and Comparative Examples 3 to 8

Preparation of a Mini-Tablet Forming a Second Enteric Coating Layer

Using the compositions of Tables 4 and 5 below in a fluidized bed granulator, the inner-coated mini-tablet of Preparation Example 1 was coated, so as to prepare mini-tables of Examples 4 to 7 and Comparative Examples 3 to 8 forming a second enteric coating layer.

In Examples 4 and 5, a mixture of Eudragit S-100 and Eudragit L-100 mixed at a ratio of 2:1 was coated at a weight ratio of 25% (w/w) to 35% (w/w) with respect to the inner-coated mini-tablet. In Examples 6 and 7, a mixture of Eudragit S-100 and L-100 mixed at a ratio of 3:1 was coated at a weight ratio of 20% (w/w) to 30% (w/w) with respect to the inner-coated mini-tablet.

TABLE 4

Compositions of second enteric coating layers of Examples 4 to 7

| | Weight (mg/10 tablets) | | | |
|---|---|---|---|---|
| | Eudragit S/L = 2/1 | | Eudragit S/L = 3/1 | |
| Ingredient | Example 4 | Example 5 | Example 6 | Example 7 |
| Eudragit S-100 | 13.3 | 18.6 | 12.0 | 18.0 |
| Eudragit L-100 | 6.7 | 9.4 | 4.0 | 6.0 |
| Triethyl citrate | 2.0 | 2.8 | 1.6 | 2.4 |
| Talc | 10.0 | 14.0 | 8.0 | 12.0 |
| Ethanol | (q.s.) | (q.s.) | (q.s.) | (q.s.) |
| Purified water | (q.s.) | (q.s.) | (q.s.) | (q.s.) |
| Sum | 110.8 | 123.6 | 104.4 | 117.2 |

In Comparative Examples 3 and 4, a mixture of Eudragit S-100 and Eudragit L-100 mixed at a ratio of 2:1 was coated at a weight of 10.15% (w/w) and 40.61% (w/w), respectively, with respect to the inner-coated mini-tablet. In Comparative Examples 5 and 6, a mixture of Eudragit S-100 and Eudragit L-100 mixed at a ratio of 3:1 was coated at a weight of 10.15% (w/w) and 40.61% (w/w), respectively, with respect to the inner-coated mini-tablet. In Comparative Examples 7 and 8, a mixture of Eudragit S-100 and Eudragit L-100 mixed at a ratio of 6:1 was coated at a weight of 10.15% (w/w) and 20.30% (w/w), respectively, with respect to the inner-coated mini-tablet.

TABLE 5

Compositions of second enteric coating layers of Comparative Examples 3 to 8

| | Weight (mg/10 tablets) | | | | | |
|---|---|---|---|---|---|---|
| | Eudragit S/L = 2/1 | | Eudragit S/L = 3/1 | | Eudragit S/L = 6/1 | |
| Ingredient | Comparative Example 3 | Comparative Example 4 | Comparative Example 5 | Comparative Example 6 | Comparative Example 7 | Comparative Example 8 |
| Eudragit S-100 | 5.3 | 21.2 | 6.0 | 24.0 | 6.86 | 13.7 |
| Eudragit L-100 | 2.7 | 10.8 | 2.0 | 8.0 | 1.14 | 2.3 |
| Triethyl citrate | 0.8 | 3.2 | 0.8 | 3.2 | 0.8 | 1.6 |
| Talc | 4.0 | 16.0 | 4.0 | 16.0 | 4.0 | 8.0 |
| Ethanol | (q.s.) | (q.s.) | (q.s.) | (q.s.) | (q.s.) | (q.s.) |
| Purified water | (q.s.) | (q.s.) | (q.s.) | (q.s.) | (q.s.) | (q.s.) |
| Sum | 91.6 | 130.0 | 91.6 | 130.0 | 91.6 | 104.4 |

Preparation Example 4: Examples 8 and 9 and Comparative Example 9

Preparation of a Mini-Tablet Forming a First Enteric Coating Layer and a Mini-Tablet Forming a Second Enteric Coating Layer A gelatin hard capsule No. 2 whose main base material is gelatin was filled with 10 tablets of the first enteric coating layer-forming mini-tablets of Example 1 and 10 tablets of the second enteric coating layer-forming mini-tablets of Example 4 together, so as to prepare the composite capsule of Example 8 (including 40 mg of esomeprazole). In the same manner, the mini-tablets of Examples 1 and 7 filled a capsule, so as to prepare the composite capsule of Example 9. In addition, in the same manner, the mini-tablets of Example 1 and Comparative Example 3 filled a capsule, so as to prepare the composite capsule of Comparative Example 9.

Preparation Example 5: Preparation of Composite Capsules According to Capsule Types A composite capsule was prepared in the same manner as in Preparation Example 4, except that the mini-tables filled a hypromellose capsule which is a hard capsule whose main base material is hypromellose. In addition, a composite capsule was prepared in the same manner as in Preparation Example 4, except that the mini-tablets filled a pullulan capsule which is a hard capsule whose main base material is pullulan.

Experimental Example 1: Dissolution Test of First Enteric Coating Layer-Forming Mini-Tablets Using the first enteric coating layer-forming mini-tablets of Examples 1 to 3 and Comparative Examples 1 and 2, time-dependent dissolution rates of esomeprazole magnesium salts were measured under the following conditions:

Dissolution Conditions
Eluate: 300 mL of 0.01 N HCl (2 hours)→1,000 mL of artificial intestinal fluid (pH 6.8)
Apparatus: USP paddle (method), 100 rpm
Temperature: 37° C.
Time at which dissolution rates were measured: 60 minutes, 120 minutes, 125 minutes, 130 minutes, 135 minutes, 150 minutes, 165 minutes, and 180 minutes Analysis Conditions
Device in use: HPLC (Hitachi 5000 series, Japan)
Detector: Ultraviolet spectrophotometer (measured wavelength: 302 nm)
Column: Stainless steel tube having an inner diameter of about 4.0 mm and a length of about 10 cm
5 μm column filled with silica gel for liquid chromatography
Mobile Phase
Sodium phosphate buffer (pH 7.3):acetonitrile:purified water=50:35:15
Flow rate: 1.0 mL/minute
Column temperature: 30° C.

The results of the dissolution rate measurement of the first enteric coating layer-forming mini-tablets of Examples 1 to 3 are shown in Table 6 and FIG. 2

TABLE 6

| | Dissolution rate (%) | | | | | |
|---|---|---|---|---|---|---|
| | Example 1 | | Example 2 | | Example 3 | |
| Time (minute) | Mean | Standard deviation | Mean | Standard deviation | Mean | Standard deviation |
| 0 | 0.0 | 0.0 | 0.0 | 0.0 | 0.0 | 0.0 |
| 60 | 0.0 | 0.0 | 0.0 | 0.0 | 0.0 | 0.0 |
| 120 | 0.0 | 0.0 | 0.0 | 0.0 | 0.0 | 0.0 |
| 125 | 50.7 | 6.9 | 70.8 | 2.7 | 30.6 | 3.8 |
| 130 | 86.4 | 1.5 | 95.9 | 1.1 | 61.0 | 1.8 |
| 135 | 100.3 | 1.3 | 100.6 | 0.3 | 85.1 | 1.9 |
| 150 | 100.0 | 1.9 | 99.8 | 0.6 | 95.6 | 1.2 |
| 165 | 100.1 | 1.2 | 101.1 | 1.4 | 100.6 | 1.3 |
| 180 | 100.9 | 1.3 | 101.3 | 0.8 | 100.0 | 1.0 |

As shown in Table 6 and FIG. 2, the mini-tablets of Examples 1 to 3 had acid resistance in the 0.1 N HCl for the first 2 hours. Then, the mini-tablets showed a dissolution rate of 90% or more in the artificial intestinal fluid (pH 6.8) for 30 minutes (i.e., 150 minutes after the initiation of the dissolution test), indicating that the mini-tablets exhibited an immediate release.

The results of the dissolution rate measurement of Comparative Examples 1 and 2 are shown in Table 7 and FIG. 3.

TABLE 7

| | Dissolution rate (%) | | | |
|---|---|---|---|---|
| | Comparative Example 1 | | Comparative Example 2 | |
| Time (minute) | Mean | Standard deviation | Mean | Standard deviation |
| 0 | 0.0 | 0.0 | 0.0 | 0.0 |
| 60 | 0.0 | 0.0 | 0.0 | 0.0 |
| 120 | 10.0 | 6.4 | 0.0 | 0.0 |
| 125 | 65.4 | 2.7 | 10.6 | 1.8 |
| 130 | 86.9 | 3.6 | 30.3 | 4.8 |
| 135 | 89.9 | 1.5 | 61.8 | 1.3 |
| 150 | 90.6 | 0.8 | 85.6 | 1.2 |
| 165 | 90.2 | 1.1 | 95.7 | 0.5 |
| 180 | 90.1 | 0.9 | 100.7 | 0.8 |

As shown in Table 7 and FIG. 3, the mini-tablet of Comparative Example 1 in which Eudragit L30 D-55 was used as the first enteric coating layer at a weight of 4% (w/w) with respect to the inner-coated mini-tablet was difficult to have sufficient acid resistance due to the low coating ratio compared to the inner-coated mini-tablet, and showed 10% release in the 0.1 N HCl in 120 minutes. In addition, the mini-tablet of Comparative Example 1 did not show a final dissolution rate of 100% due to the characteristics of esomeprazole which is degraded in an acidic environment.

In addition, the mini-tablet of Comparative Example 2 in which Eudragit L30 D-55 was used as the first enteric coating layer at a weight of 51% (w/w) with respect to the inner-coated mini-tablet secured sufficient acid resistance, but showed a dissolution rate of 85% in 150 minutes. Therefore, the absorption of esomeprazole was slowed down, and accordingly, the expression of medical efficacy was also possibly delayed.

Experimental Example 2: Acid Resistance Test of First Enteric Coating Layer-Forming Mini-Tablets Using the first enteric coating layer-forming mini-tablets of Examples 1 to 3 and Comparative Examples 1 and 2, the mini-tablets were left for 2 hours under the acid resistance conditions described below, and the acid resistance was measured based on the amounts of esomeprazole magnesium salts. 10 mini-tablets were used, and the results are shown in Table 8.

Acid Resistance Conditions
Test solution: 0.01 N HCl
Apparatus: USP paddle method, 100 rpm
Temperature: 37° C.
Time: Leave for 2 hours
Analysis Conditions
Device in use: HPLC (Hitachi 5000 series, Japan)
Detector: Ultraviolet spectrophotometer (measured wavelength: 302 nm)
Column: Stainless steel tube having an inner diameter of about 4.0 mm and a length of about 10 cm
5 μm column filled with silica gel for liquid chromatography
Mobile Phase
Sodium phosphate buffer (pH 7.3):acetonitrile:purified water=50:35:15
Flow rate: 1.0 mL/minute
Column temperature: 30° C.

TABLE 8

| Results of the acid resistance test | | |
|---|---|---|
| | Amount before test (%) | Amount after test (%) |
| Example 1 | 100.9 ± 1.3 | 101.2 ± 0.5 |
| Example 2 | 101.3 ± 2.5 | 100.6 ± 1.2 |
| Example 3 | 100.6 ± 0.9 | 100.1 ± 1.1 |
| Comparative Example 1 | 100.6 ± 1.6 | 90.4 ± 2.4 |
| Comparative Example 2 | 100.7 ± 0.7 | 101.3 ± 1.7 |

As a result of the acid resistance test in 0.1 N HCl of Examples 1 to 3 and Comparative Examples 1 and 2 as shown in Table 8, Comparative Example 1 in which the ratio of the coating layer was low showed a difference of about 10.0% in the amounts of esomeprazole magnesium salt before and after the test. However, the remaining samples except for Comparative Example 1 were found to have the amounts similar to the original active ingredient amounts after the acid resistance test.

Experimental Example 3: Dissolution Test of Second Enteric Coating Layer-Forming Mini-Tablets Using the second enteric coating layer-forming mini-tablets of Examples 4 to 7 and Comparative Examples 3 to 8, time-dependent dissolution rates of esomeprazole magnesium salts were measured under the following conditions:

Dissolution Conditions
Eluate: 300 mL of 0.01 N HCl→1,000 mL of artificial intestinal fluid (pH 6.8)
Apparatus: USP paddle (method), 100 rpm
Temperature: 37° C.
Time at which dissolution rates were measured: 60 minutes, 120 minutes, 150 minutes, 180 minutes, 210 minutes, 240 minutes, 300 minutes, and 360 minutes
Analysis Conditions
Device in use: HPLC (Hitachi 5000 series, Japan)
Detector: Ultraviolet spectrophotometer (measured wavelength: 302 nm)
Column: Stainless steel tube having an inner diameter of about 4.0 mm and a length of about 10 cm
5 μm column filled with silica gel for liquid chromatography
Mobile Phase
Sodium phosphate buffer (pH 7.3):acetonitrile:purified water=50:35:15
Flow rate: 1.0 mL/minute
Column temperature: 30° C.

The results of the dissolution rate measurement of the second enteric coating layer-forming mini-tablets of Examples 4 to 7 are shown in Table 9 and FIG. 4.

TABLE 9

| Time (minutes) | Example 4 | | Example 5 | | Example 6 | | Example 7 | |
|---|---|---|---|---|---|---|---|---|
| | Mean | Standard deviation | Mean | Standard deviation | Mean | Standard deviation | Mean | Standard deviation |
| 0 | 0.0 | 0.0 | 0.0 | 0.0 | 0.0 | 0.0 | 0.0 | 0.0 |
| 60 | 0.0 | 0.0 | 0.0 | 0.0 | 0.0 | 0.0 | 0.0 | 0.0 |
| 120 | 0.0 | 0.0 | 0.0 | 0.0 | 0.0 | 0.0 | 0.0 | 0.0 |
| 150 | 0.0 | 0.0 | 0.0 | 0.0 | 0.0 | 0.0 | 0.0 | 0.0 |
| 180 | 0.0 | 0.0 | 0.0 | 0.0 | 1.8 | 3.1 | 0.0 | 0.0 |
| 240 | 64.6 | 2.1 | 0.0 | 0.0 | 65.5 | 2.6 | 5.9 | 1.5 |
| 300 | 94.4 | 0.2 | 76.4 | 7.7 | 83.2 | 6.6 | 51.1 | 9.7 |
| 360 | 1-1.2 | 2.1 | 98.8 | 2.0 | 99.2 | 9.7 | 101.7 | 11.1 |

Referring to the results of Table 9 and FIG. 4, the mini-tablets of Examples 4 to 7 did not show any dissolution for the first 2 hours in 0.1 N HCl so that the acid resistance was secured. Then, the release of the drugs was delayed for 60 minutes or longer in the artificial intestinal fluid (pH 6.8). However, once the release of the drugs started, the release was rapidly done.

In spite of slight differences depending on the ratio of Eudragit S and Eudragit L, after the acid resistance in 0.1 N HCl was secured for 120 minutes, esomeprazole magnesium salt was hardly released for 60 minutes in the artificial intestinal fluid, but was rapidly released at the elapsed time of 60 minutes. Then, at the elapsed time of 360 minutes, excellent releasing characteristics that 99% or more of esomeprazole magnesium salt was released were confirmed. When the dissolution rate of 90% or more was not secured at the time of 360 minutes due to the nature of the formulation, the drug may be possibly discharged without being dissolved, and in this regard, it was confirmed that sufficient release can be achieved in Examples 4 to 7.

In addition, the results of the dissolution rate measurement of the second enteric coating layer-forming mini-tablets of Comparative Examples 3 to 8 are shown in Table 10 and FIG. 5.

the drug release of more than 90% was not achieved even after 6 hours had elapsed, and thus, the drugs may be possibly excreted without the release of the drugs is not sufficiently performed.

Experimental Example 4: Dissolution Rate Test of Composite Capsules

Using the composite capsules of Examples 8 and 9 and Comparative Example 9, time-dependent dissolution rates of esomeprazole magnesium salts were measured under the following conditions:

Dissolution Conditions
Eluate: 300 mL of 0.1N HCl→1,000 mL of artificial intestinal fluid (pH 6.8)
Apparatus: USP paddle (method), 100 rpm
Temperature: 37° C.
Time at which dissolution rates were measured: 60 minutes, 120 minutes, 125 minutes, 130 minutes, 135 minutes, 150 minutes, 165 minutes, 180 minutes, 210 minutes, 240 minutes, 300 minutes, and 360 minutes
Analysis Conditions
Device in use: HPLC (Hitachi 5000 series, Japan)

TABLE 10

| Time (minute) | Comparative Example 3 | | Comparative Example 4 | | Comparative Example 5 | | Comparative Example 6 | | Comparative Example 7 | | Comparative Example 8 | |
|---|---|---|---|---|---|---|---|---|---|---|---|---|
| | Mean | Standard deviation | Mean | Standard deviation | Mean | Standard deviation | Mean | Standard deviation | Mean | Standard deviation | Mean | Standard deviation |
| 0 | 0.0 | 0.0 | 0.0 | 0.0 | 0.0 | 0.0 | 0.0 | 0.0 | 0.0 | 0.0 | 0.0 | 0.0 |
| 60 | 0.0 | 0.0 | 0.0 | 0.0 | 0.0 | 0.0 | 0.0 | 0.0 | 0.0 | 0.0 | 0.0 | 0.0 |
| 120 | 0.0 | 0.0 | 0.0 | 0.0 | 0.5 | 0.3 | 0.0 | 0.0 | 0.0 | 0.0 | 0.0 | 0.0 |
| 150 | 52.9 | 0.0 | 0.0 | 0.0 | 25.6 | 2.6 | 0.0 | 0.0 | 16.7 | 3.1 | 0.0 | 0.0 |
| 180 | 756. | 10.6 | 0.0 | 0.0 | 65.1 | 13.8 | 0.0 | 0.0 | 33.5 | 4.0 | 0.0 | 0.0 |
| 210 | 86.4 | 2.3 | 0.0 | 0.0 | 74.1 | 3.2 | 0.0 | 0.0 | 52.4 | 3.0 | 0.0 | 0.0 |
| 240 | 93.6 | 7.0 | 0.0 | 0.0 | 82.1 | 4.8 | 0.0 | 0.0 | 62.6 | 4.2 | 3.0 | 5.1 |
| 300 | 99.0 | 1.1 | 0.0 | 0.0 | 96.0 | 10.1 | 0.0 | 0.0 | 87.8 | 8.2 | 44.5 | 8.0 |
| 360 | 91.5 | 0.8 | 56.4 | 7.5 | 100.4 | 3.9 | 16.5 | 2.3 | 95.8 | 9.3 | 61.2 | 6.2 |

Referring to the results shown in Table 10 and FIG. 5, in the case of the mini-tablets of Comparative Examples 3, 5, and 7, it was difficult to secure acid resistance in 0.1 N HCl for 2 hours due to the low weight ratio of the second enteric coating layer. In the case of the mini-tablets of Comparative Examples 4, 6, and 8, due to the high weight ratio of the second enteric coating layer, not only the acid resistance was secured, but also the release of the drugs was excessively delayed in the artificial intestinal fluid. In these mini-tablets, Detector: Ultraviolet spectrophotometer (measured wavelength: 302 nm)
Column: Stainless steel tube having an inner diameter of about 4.0 mm and a length of about 10 cm
5 μm column filled with silica gel for liquid chromatography
Mobile Phase
Sodium phosphate buffer (pH 7.3):acetonitrile:purified water=50:35:15

Flow rate: 1.0 mL/minute
Column temperature: 30° C.

The results of the dissolution rate measurement are shown in Table 11 and FIG. 6.

TABLE 11

Dissolution rates of esomeprazole magnesium salt

| | Dissolution rate (%) | | | | | |
|---|---|---|---|---|---|---|
| | Example 8 | | Example 9 | | Comparative Example 9 | |
| Time (minute) | Mean | Standard deviation | Mean | Standard deviation | Mean | Standard deviation |
| 0 | 0.0 | 0.0 | 0.0 | 0.0 | 0.0 | 0.0 |
| 60 | 0.0 | 0.0 | 0.0 | 0.0 | 0.0 | 0.0 |
| 120 | 0.0 | 0.0 | 0.0 | 0.0 | 0.0 | 0.0 |
| 125 | 22.8 | 5.6 | 24.8 | 4.5 | 25.2 | 4.5 |
| 130 | 45.1 | 1.3 | 44.2 | 2.2 | 46.3 | 2.2 |
| 135 | 50.1 | 0.9 | 49.9 | 1.0 | 50.1 | 1.0 |
| 150 | 50.0 | 0.8 | 50.0 | 1.2 | 75.3 | 2.4 |
| 165 | 50.2 | 1.1 | 50.4 | 0.6 | 86.7 | 1.9 |
| 180 | 50.0 | 0.5 | 50.3 | 0.5 | 98.6 | 7.8 |
| 210 | 53.5 | 8.5 | 53.3 | 10.6 | 100.4 | 4.9 |
| 240 | 82.6 | 2.3 | 94.1 | 8.3 | 100.1 | 6.8 |
| 300 | 95.5 | 1.9 | 99.3 | 1.5 | 99.1 | 2.7 |
| 360 | 101.2 | 1.2 | 100.7 | 2.0 | 98.6 | 1.9 |

Referring to the results of Table 11 and FIG. 6, the composite capsules of Examples 8 and 9 prepared by mixing the mini-tablet including the first enteric coating layer and the mini-tablet including the second enteric coating layer at a ratio of 1:1 secured the acid resistance for the first 2 hours in 0.1N HCl. Then, after the first release in the artificial intestinal fluid, the release was delayed for about 45 minutes before the start of the second release. Referring to the graph of FIG. 6, such double release characteristics have been clearly identified. Therefore, the composite capsules of Examples 8 and 9 showed sustained release of the drugs for up to 6 hours after the start of the dissolution test due to the double release characteristics in the artificial intestinal fluid.

In the mini-tablet of Comparative Example 9, the acid resistance was secured in 0.1 N HCl for 2 hours. However, after the first release, the release of the drugs occurred immediately without delay in the release before the start of the second release. Thus, the release of most drugs (98% or more) was completed after 3 hours of the dissolution test.

While the present invention has been particularly shown and described with reference to exemplary embodiments thereof, it will be understood by those skilled in the art that various changes in form and details may be made therein without departing from the spirit and scope of embodiments as defined by the appended claims. The exemplary embodiments should be considered in descriptive sense only and not for purposes of limitation. Therefore, the scope of embodiments is defined not by the detailed description of embodiments but by the appended claims, and all differences within the scope will be construed as being included in the present invention.

The invention claimed is:

1. A composite capsule comprising:
a first dissolving part comprising a core comprising, as an active ingredient, esomeprazole or a pharmaceutically acceptable salt thereof, an inner coating layer on the core, and a first enteric coating layer on the inner coating layer; and
a second dissolving part comprising a core comprising, as an active ingredient, esomeprazole or a pharmaceutically acceptable salt thereof, an inner coating layer on the core, and a second enteric coating layer on the inner coating layer,
wherein the first enteric coating layer comprises, as a coating base material, methacrylic acid copolymer LD in an amount of about 5% (w/w) to about 50% (w/w) of the core on which the inner coating layer is formed,
the second enteric coating layer comprises, as a coating base material, a mixture containing methacrylic acid copolymer S and methacrylic acid copolymer L at a ratio of about 1.5:1 (w/w) to about 3.5:1 (w/w) in an amount of about 15% (w/w) to about 40% (w/w) of the core on which the inner coating layer is formed,
wherein the cores of the first dissolving part and the second dissolving part are all mini-tablets,
wherein the inner coating layer is on the core and is contained in an amount of about 3% (w/w) to about 5% (w/w) of the core on which the inner coating layer is formed, and
wherein, in an artificial intestinal fluid having a pH of 6.7 to 6.9 and a temperature of 37±0.5° C., the active ingredient of the first dissolving part releases into the artificial intestinal fluid before the active ingredient of the second dissolving part releases.

2. The composite capsule of claim 1, wherein the second enteric coating layer comprises, as a coating base material, a mixture containing methacrylic acid copolymer S and methacrylic acid copolymer L at a ratio of about 2:1 (w/w) to about 3:1 (w/w) in an amount of about 20% (w/w) to about 35% (w/w) of the core on which the inner coating layer is formed.

3. The composite capsule of claim 1, wherein the inner coating layer comprises one or more coating base materials selected from hydroxypropyl methylcellulose (HPMC), polyvinylpyrrolidone (PVP), low-substituted hydroxypropyl cellulose (HPC-L), starch, gelatin, ethyl cellulose (EC), and a combination thereof.

4. The composite capsule of claim 1, wherein the first dissolving part and the second dissolving part each comprise, as a free base, esomeprazole or a pharmaceutically acceptable salt thereof at a weight ratio in a range of about 2:1 to about 1:3.

5. The composite capsule of claim 1, wherein the cores of the first dissolving part and the second dissolving part each comprise one or more pharmaceutical additives selected from a diluent, a binder, a disintegrant, a lubricant, a surfactant, an anti-oxidant, a preservative, a stabilizer, and a combination thereof.

6. The composite capsule of claim 1, wherein, when a dissolution test is continuously conducted for 240 minutes in an artificial intestinal fluid having a pH of 6.7 to 6.9 following dissolution in 0.1 N HCl aqueous solution at 100 revolutions per minutes (rpm) for 120 minutes at a temperature of 37±0.5° C. according to paddle method II described in the United States Pharmacopeia (USP),
the composite capsule has acid resistance in 0.1 N HCl for 120 minutes,
about 55% or less of the active ingredient is dissolved in the artificial intestinal fluid for 60 minutes, and
about 95% or more of the active ingredient is dissolved in the artificial intestinal fluid for 240 minutes.

7. The composite capsule of claim 1, wherein the pharmaceutically acceptable salt of esomeprazole comprises an esomeprazole magnesium salt or an esomeprazole strontium salt.

8. The composite capsule of claim 1, wherein a capsule base material of the composite capsule is selected from gelatin, hypromellose, pullulan, polyvinyl alcohol, and a combination thereof.

9. The composite capsule of claim 1, wherein the composite capsule is for the prevention or treatment of diseases related to hypersecretion of gastric acid selected from gastroesophageal reflux disease, gastritis, duodenitis, gastric ulcer, duodenal ulcer, and peptic ulcer.

10. The composite capsule of claim 1, wherein the composite capsule is administered once a day.

11. A method of preparing the composite capsule of claim 1, the method comprising:
preparing a core comprising esomeprazole or a pharmaceutically acceptable salt thereof, and a pharmaceutical additive;
coating the core with an inner coating layer;
obtaining a first dissolving part by coating a first enteric coating layer on the inner coating layer;
separately, obtaining a second dissolving part by coating a second enteric coating layer on the inner coating layer; and
filling a capsule with the first dissolving part and the second dissolving part together to thereby prepare the composite capsule, wherein the first enteric coating layer comprises, as a coating base material, methacrylic acid copolymer LD in an amount of about 5% (w/w) to about 50% (w/w) of the core on which the inner coating layer is formed, the second enteric coating layer comprises, as a coating base material, a mixture containing methacrylic acid copolymer S and methacrylic acid copolymer L at a ratio of about 1.5:1 (w/w) to about 3.5:1 (w/w) in an amount of about 15% (w/w) to about 40%(w/w) of the core on which the inner coating layer, wherein the cores of the first dissolving part and the second dissolving part are all mini-tablets, wherein the inner coating layer is on the core and is contained in an amount of about 3% (w/w) to about 5% (w/w) of the core on which the inner coating layer is formed, and wherein, in an artificial intestinal fluid having a pH of 6.7 to 6.9 and a temperature of 37±0.5° C., the active ingredient of the first dissolving part releases into the artificial intestinal fluid before the active ingredient of the second dissolving part releases.

* * * * *